United States Patent
Bailey

Patent Number: 5,947,120
Date of Patent: Sep. 7, 1999

[54] MEDICATION ADMINISTERING APPARATUS FOR USE WITH AN ENDOTRACHEAL TUBE

[76] Inventor: William A. Bailey, Rte. 4 Box 658, Stuart, Va. 24171

[21] Appl. No.: 08/850,267
[22] Filed: May 5, 1997
[51] Int. Cl.$^6$ .................................................. A61M 16/00
[52] U.S. Cl. ........................ 128/207.14; 128/207.15; 128/200.26; 128/200.24; 128/911; 128/912
[58] Field of Search ........................ 128/200.26, 200.24, 128/207.14, 207.15, 911, 912, DIG. 26; 604/93

[56] References Cited

U.S. PATENT DOCUMENTS

| | | | |
|---|---|---|---|
| 4,146,034 | 3/1979 | Gupta | 128/207.14 |
| 4,152,017 | 5/1979 | Abramson | 128/207.14 |
| 4,219,912 | 9/1980 | Adams. | |
| 4,346,702 | 8/1982 | Kubota | 128/207.14 |
| 4,520,812 | 6/1985 | Freitag et al. | 128/204.25 |
| 4,919,127 | 4/1990 | Pell | 128/207.14 |
| 5,016,614 | 5/1991 | MacAllister | 128/207.14 X |
| 5,101,817 | 4/1992 | Etter | 128/207.14 X |
| 5,163,902 | 11/1992 | Lynn et al. . | |
| 5,220,916 | 6/1993 | Russo | 128/207.16 |
| 5,330,448 | 7/1994 | Chu . | |
| 5,344,414 | 9/1994 | Lopez et al. . | |
| 5,395,348 | 3/1995 | Ryan . | |
| 5,588,424 | 12/1996 | Insler et al. | 128/207.15 |
| 5,598,840 | 2/1997 | Iund et al. | 128/207.14 |
| 5,642,726 | 7/1997 | Owens et al. | 128/200.26 |
| 5,642,730 | 7/1997 | Baran | 128/207.14 |
| 5,655,526 | 8/1997 | Gibertoni | 128/205.27 |
| 5,730,123 | 3/1998 | Lorenzen et al. | 128/207.14 |

FOREIGN PATENT DOCUMENTS

0245119  11/1987  European Pat. Off. ............... 128/912

OTHER PUBLICATIONS

Portex "Jet Ventilator Adaptor" specification, Jun. 6, 1994.

Primary Examiner—Mickey Yu
Assistant Examiner—Dinh X. Nguyen
Attorney, Agent, or Firm—David L. Volk

[57] ABSTRACT

A substantially tubular body includes an open first end adapted for connection to a ventilator. The body further includes an open second end opposite the first end and adapted for connection to an endotracheal tube. An injection tube has a primary end and a secondary end. A pre-pierced, self-sealing injection port is disposed at the primary end of the injection tube and is adapted for insertion of the needle there-through and into the injection tube. The secondary end is connected to the body between the first end and the second end, whereby medication delivered through a needle inserted through the primary end will flow through the injection tube, into the body, then into the endotracheal tube, and will be atomized into a patient's lungs when the ventilator forces air through the endotracheal tube.

3 Claims, 5 Drawing Sheets

1

MEDICATION ADMINISTERING APPARATUS FOR USE WITH AN ENDOTRACHEAL TUBE

BACKGROUND OF THE INVENTION

1. Field of the Invention

The present invention relates to medical devices, particularly to medication administering apparatus with self-sealing ports.

2. Description of the Related Art

When a patient is in cardiac arrest, breathing stops and the patient must be ventilated with a mechanical ventilator or bag ventilator attached to an endotracheal tube. The endotracheal tube is inserted through the patient's nose or mouth into the trachea. Air from the ventilator flows through the endotracheal tube and fills the patient's lungs.

Certain medications such as Epinephrine and Lidocaine are indicated for administration during cardiac arrest. Often, these medications are administered through the endotracheal tube, particularly if the patient is not already attached to an IV. Administering medication through the endotracheal tube is easier than trying to find a vein and insert a syringe. A problem with administration of medication through the endotracheal tube is that it requires removal of the ventilator or bag from the end of the tube, in order to squirt in the medication from a syringe through the end of the tube and subsequently into the lungs. This procedure interrupts ventilation. During chest compressions, the medication and other body fluids may be sprayed back out of the tube, compromising body substance isolation protocols.

What is needed is an apparatus which would allow for medication to be administered through an endotracheal tube without interrupting the ventilation process, and without spraying of the medication and bodily fluids back out of the tube.

SUMMARY OF THE INVENTION

The medication administering apparatus for use with an endotracheal tube of the present invention includes a substantially tubular body having an open first end adapted for connection to a ventilator. The body further includes an open second end opposite the first end and adapted for connection to the endotracheal tube. An injection tube has a primary end and a secondary end. A pre-pierced, self-sealing injection port is disposed at the primary end of the injection tube and is adapted for insertion of a needle there-through and into the injection tube. The secondary end is connected to the body between the first end and the second end, whereby medication delivered through the needle inserted through the primary end will flow through the injection tube, into the body, into the endotracheal tube, and will be atomized into a patient's lungs when the ventilator forces air through the endotracheal tube.

In one embodiment, the body tapers from a first diameter between the first and second ends to a second diameter at the second end, the second diameter being smaller than the first diameter, whereby endotracheal tubes of various tube diameters may be inserted over the second end of the body and snugly fitted around the body.

DETAILED DESCRIPTION

Figure 1:
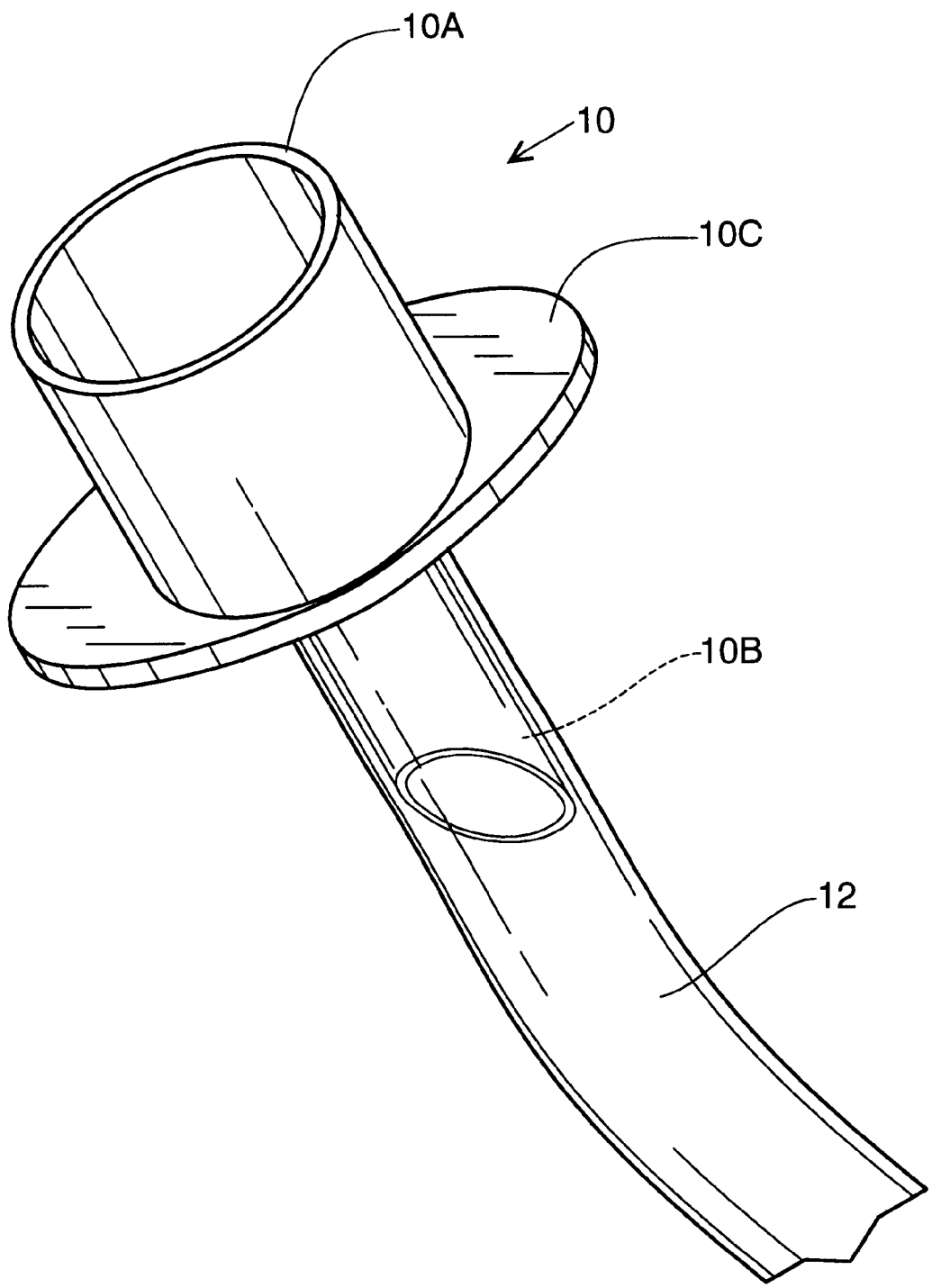
FIG. 1 is a perspective view of a ventilator adapter of the prior art, attached to an endotracheal tube.

FIG. 1 is a perspective view of a ventilator adapter 10 of the prior art, attached to an endotracheal tube 12. An adapter first end 10A is adapted for connection to a ventilator (not shown), which may be a mechanical ventilator or a bag ventilator. An adapter second end 10B is adapted for connection to the endotracheal tube 12. An adapter stop member 10C limits travel of the tube 12 along the adapter 10. Ventilators, ventilator adapters and endotracheal tubes as just described are well known in the art.

Figure 2:
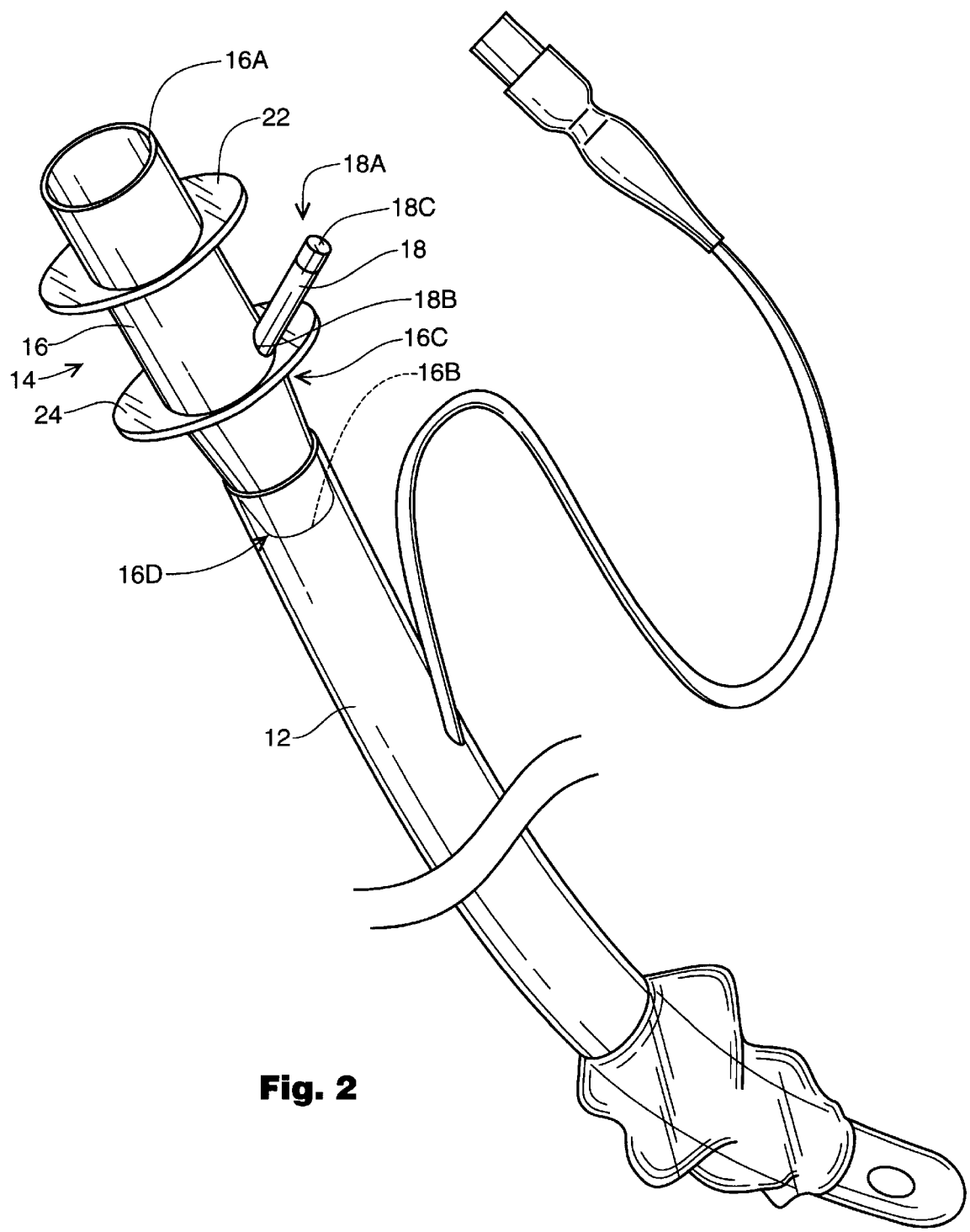
FIG. 2 is a perspective view of the medication administering apparatus of the present invention, attached to an endotracheal tube.

FIG. 2 is a perspective view of the medication administering apparatus 14 of the present invention, attached to an endotracheal tube 12. The apparatus 14 includes a substantially tubular body 16 having an open first end 16A adapted for connection to a ventilator (not shown). The first end 16A is configured the same as the adapter first end 10A of the prior art.

The body 16 further includes an open second end 16B opposite the first end 16A. The second end 16B of the body 16 is inserted into the endotracheal tube 12. When the ventilator is connected to the first end 16A, the ventilator is in fluid communication with the tube 12 through the body 16.

The body 16 tapers from a first diameter 16C between the first and second ends 16A, 16B to a second diameter 16D at the second end 16B. The second diameter 16D is smaller than the first diameter 16C; thus endotracheal tubes 12 of various tube diameters may be inserted over the second end 16B of the body 16 and snugly fitted around the body 16.

Figure 3:
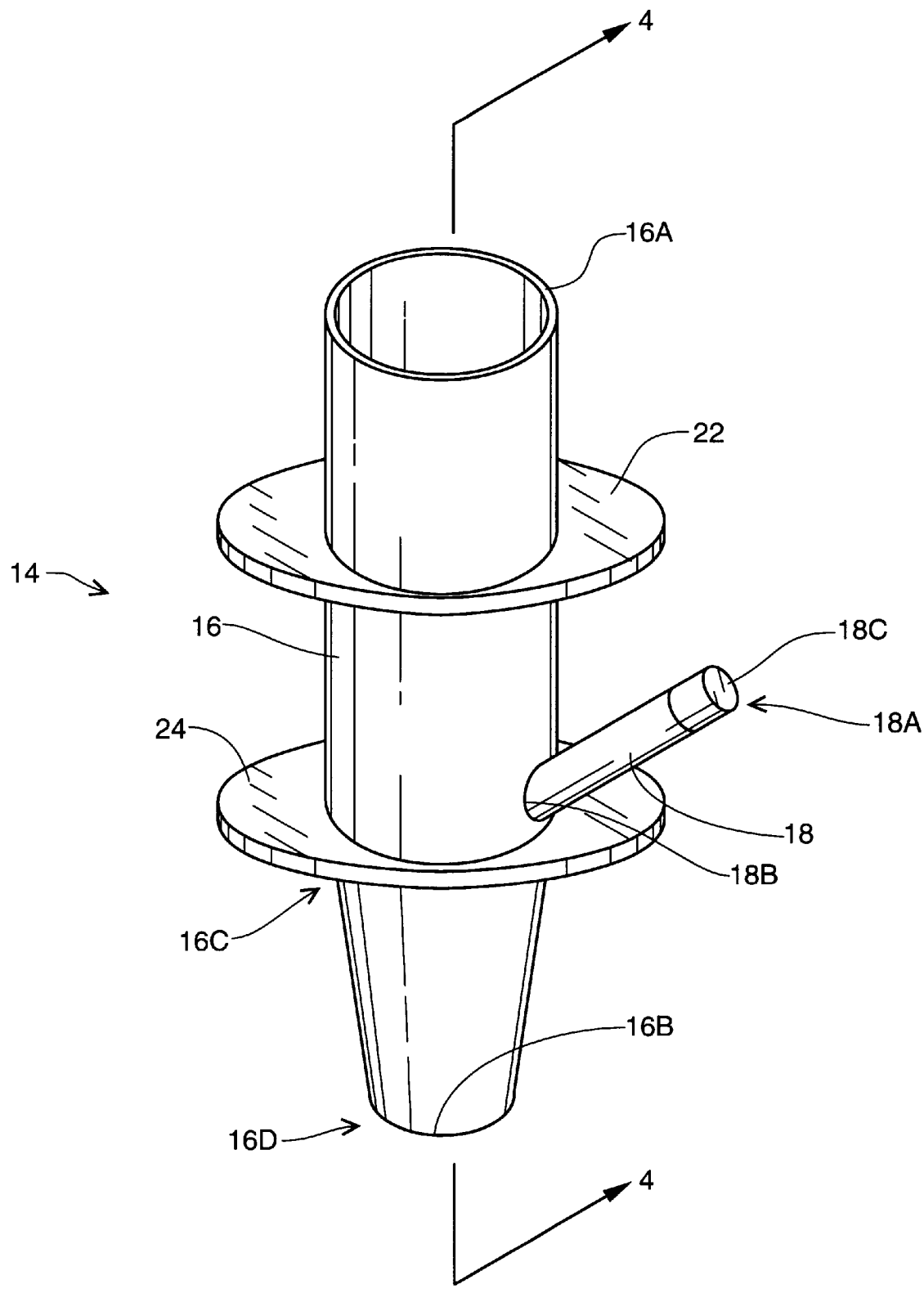
FIG. 3 is a perspective view of the apparatus of the present invention, shown without the endotracheal tube.
Figures 4, 4A:
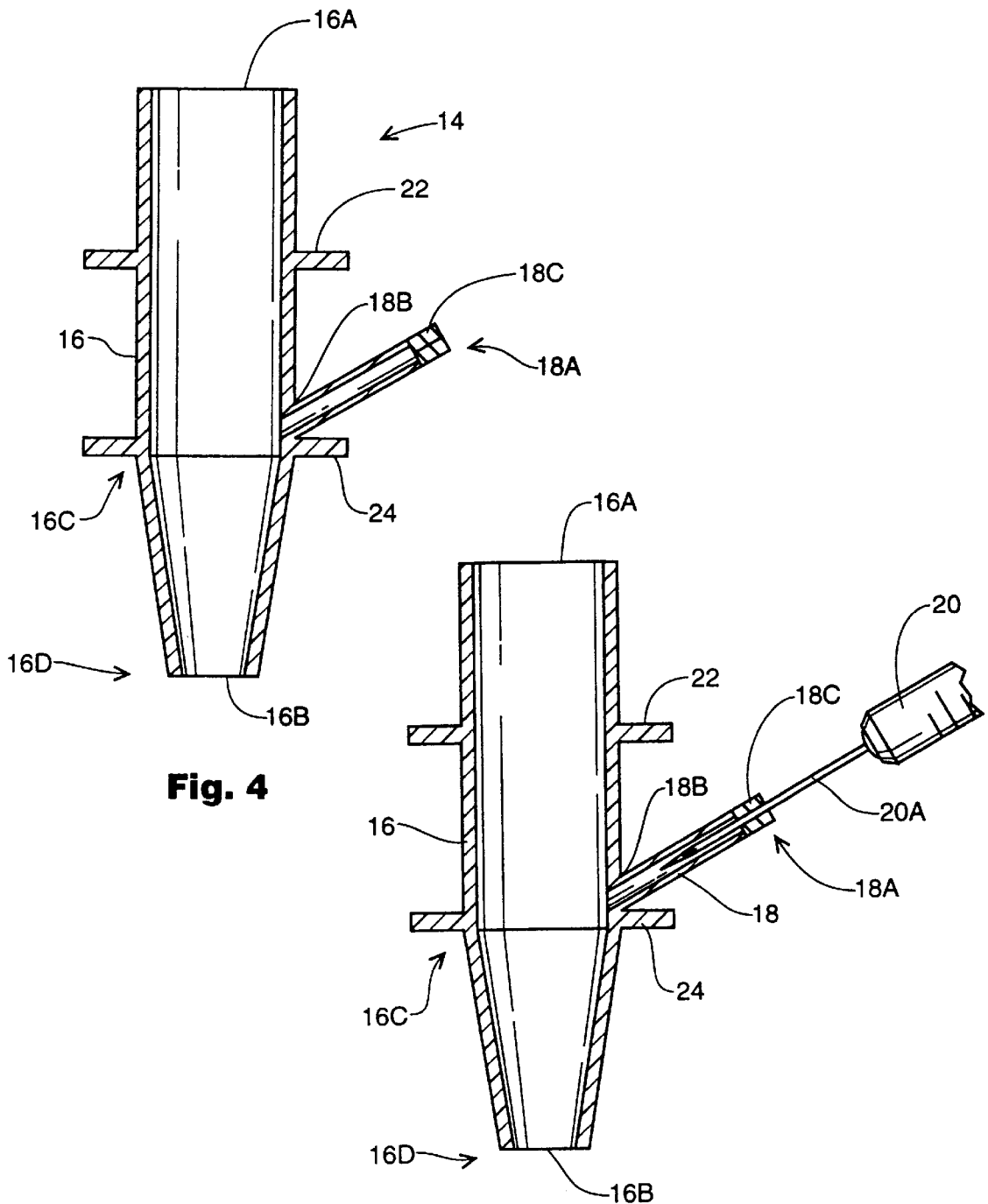
FIG. 4 is a cross-sectional view of the apparatus taken along line 4—4 of FIG. 3.
FIG. 4A is a cross-sectional view similar to FIG. 4, showing a needle of a syringe in use with the apparatus.

FIG. 3 is a perspective view of the apparatus 14 of the present invention, shown without the endotracheal tube 12. FIG. 4 is a cross-sectional view of the apparatus 14 taken along line 4—4 of FIG. 3. FIG. 4A is a cross-sectional view similar to FIG. 4, showing a needle 20A of a syringe 20 in use with the apparatus 14. Referring to FIGS. 3, 4 and 4A, an injection tube 18 has a primary end 18A and a secondary end 18B. A pre-pierced, self-sealing injection port 18C is disposed at the primary end 18A of the injection tube 18 and is adapted for insertion of the needle 20A of the syringe 20 there-through and into the injection tube 18. Pre-pierced, self-sealing injection ports are known in the prior art.

The secondary end 18B is connected to the body 16 between the first end 16A and the second end 16B; thus, medication delivered through the needle 20A will flow through the injection tube 18, into the body 16, into the endotracheal tube 12, and will be atomized into the patient's lungs when the ventilator forces air through the endotracheal tube 12.

A first stop member 22 is positioned on the body 16 between the first end 16A and the injection tube 18 to limit travel of the ventilator along the body 16. A second stop member 24 is positioned on the body 16 between the second end 16B and the injection tube 18 to limit travel of the endotracheal tube 12 along the body 16.

Figure 4B:
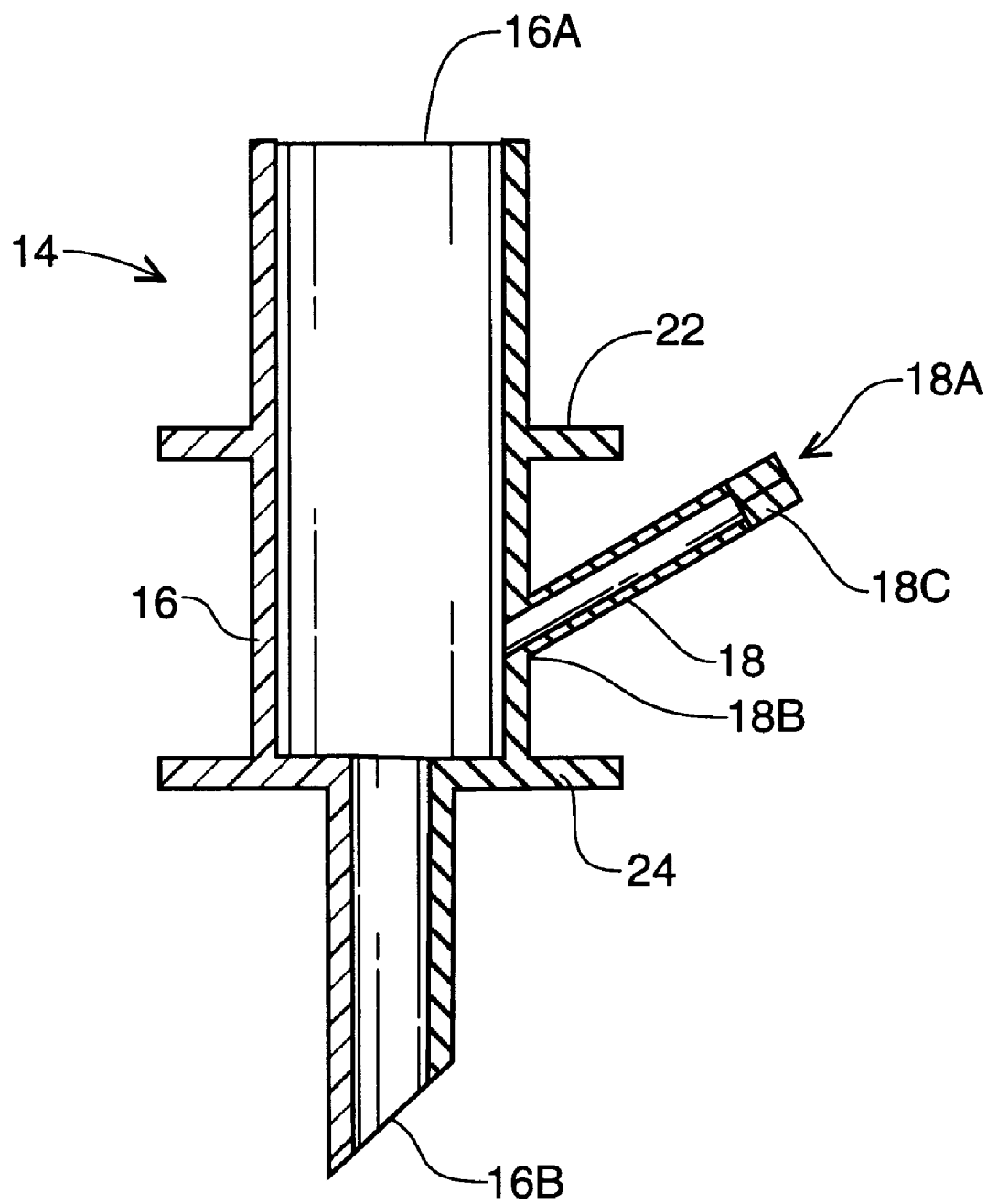
FIG. 4B is a cross-sectional view similar to FIG. 4A, showing an embodiment of the invention which eliminates the tapered portion of the body.

FIG. 4B is a cross-sectional view similar to FIG. 4A, showing an embodiment of the invention which eliminates the taper between the second end 16B and the injection tube 18. This embodiment would be limited to use with endotracheal tubes of a single diameter.

In the embodiment of FIG. 4B, the second end 16B is cut at an angle to increase the effective size of the opening at the second end 16B, to enhance flow out of the apparatus 14. This particular configuration of the second end 16B is known in the art (see FIG. 1), and may be applied to the embodiment of FIGS. 2–4A.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. Accordingly, the scope of the invention is to be limited only by the following claims and their legal equivalents.

The invention claimed is:

1. A medication apparatus for use with an endotracheal tube, the apparatus comprising:
    a. a straight tubular body having an open first end adapted for connection to a ventilator;
    b. the body further having an open second end opposite the first end and adapted for connection to the endotracheal tube;
    c. a straight injection tube having a primary end and a secondary end;
    d. an injection port pre-pierced to form a self-sealing aperture there-through, disposed at the primary end of the injection tube and adapted for insertion of a needle through the aperture and into the injection tube, a longitudinal axis of the aperture being coaxial with a longitudinal axis of the injection tube;
    e. the secondary end connected directly to the body between the first end and the second end in such a manner that the injection tube forms an acute angle with respect to the body and the secondary end is disposed between the primary end and the second end;
    f. an internal diameter of the injection tube being less than 20% of an internal diameter of the body measured where the secondary end connects to the body;
    g. a first stop member positioned on the body between the first end and the injection tube, the first stop member adapted to limit travel of the ventilator along the body; and
    h. a second stop member positioned on the body between the second end and the injection tube, the second stop member adapted to limit travel of the endotracheal tube along the body, whereby medication delivered through a needle inserted through the primary end will flow through the injection tube, into the body, then into the endotracheal tube, and will be atomized into a patient's lungs when the ventilator forces air through the endotracheal tube.

2. The medication apparatus of claim 1, wherein the body tapers from a first diameter between the first and second ends to a second diameter at the second end, the second diameter being smaller than the first diameter, whereby endotracheal tubes of various tube diameters may be inserted over the second end of the body and snugly fitted around the body.

3. The medication apparatus of claim 1, wherein each of the first and second stop members is a planar shield extending perpendicularly outwardly from opposing sides of the body.

* * * * *